United States Patent [19]

Trager

[11] Patent Number: 5,043,162

[45] Date of Patent: Aug. 27, 1991

[54] HAIR GROWTH PROMOTER

[76] Inventor: Seymour F. Trager, 14 Sherwood Dr., Plainview, N.Y. 11803

[21] Appl. No.: 577,699

[22] Filed: Sep. 5, 1990

[51] Int. Cl.⁵ .............................................. A61K 9/06
[52] U.S. Cl. ...................................... 424/401; 424/70; 514/256; 514/887; 514/880; 514/947
[58] Field of Search .................. 424/401, 70; 514/256, 514/929, 947, 969, 880

[56] References Cited

U.S. PATENT DOCUMENTS

| | | | |
|---|---|---|---|
| 4,892,890 | 1/1990 | Damani | 514/786 |
| 4,968,685 | 11/1990 | Grollier | 514/256 |
| 4,973,474 | 11/1990 | Hocguaux et al. | 424/70 |

*Primary Examiner*—Thurman K. Page
*Assistant Examiner*—David J. Colucci
*Attorney, Agent, or Firm*—Fidelman & Wolffe

[57] ABSTRACT

Compositions containing mixtures of lower alkyl nicotinate and histamine hydrochloride, particularly useful in promoting hair growth and revitalizing the hair and scalp by topical application.

6 Claims, No Drawings

HAIR GROWTH PROMOTER

This invention relates to the reduction of hair loss. More particularly, this invention relates to chemical compositions adapted to be used in different forms for scalp treatment, reduction of hair loss and stimulation of new hair growth.

It has been recognized in the prior art that certain chemicals exhibiting vasodilation properties are beneficial for stimulating the scalp by increasing bloodflow when topically applied, a number of which are also said to prevent or to slow excessive hair loss. For example, Japanese Patent No. 47-47663 teaches the use of hair tonics containing a Vitamin E ester of nicotinic acid for reducing excessive hair loss, the composition additionally containing isopropyl myristate, propylene glycol, menthol, pantothenate, Vitamin $B_6$ hydrochloride, hexachlorophene and perfume.

U.S. Pat. No. 4,329,339 discloses a composition for topical application of the reaction product of nicotinic acid, salt or halide with a polyol selected from glucose, ethylene glycol, polyethylene glycol, dipropylene glycol, propylene glycol, arabite and 4,6-0-benzidene-D-glycopyranase.

Great Britain Patent No. 1,603,609 provides for a hair and scalp conditioner containing commercial hair conditioner, carrier and one or more of Vitamins $A_1$, $B_1$, $B_2$, $B_6$, D, nicotinamide and ascorbic acid.

The combination of chenodeoxycholic acid and/or ursodeoxycholic acid and nicotinic acid for increasing circulation of blood in the scalp and preventing hair loss is described in U.S. Pat. No. 4,185,099.

U.S. Pat. No. 2,431,558 to Huber discloses a composition for topical application containing butyl, pentyl, hexyl, heptyl or octyl nicotinate, the application of the composition to the skin producing vasodilation in the region of application without significantly irritating the tissues.

While such compositions as have been described, suora, containing as they do, known vasodilators, do serve to increase bloodflow in the areas of application, such compositions have been found to be generally ineffective in stimulating hair growth and reducing excessive hair loss. Stimulation of the scalp, while beneficial to the scalp, does not carry with it stimulation of the zymogens which control hair growth.

It has been found that mixtures of lower alkyl nicotinates and histamine hydrochloride, in certain concentrations, dispensed in suitable carriers, with or without additional adjuvants, provide compositions which are extremely useful for topical application to the scalp and hair, enhancing the general appearance of the skin and hair and promoting hair growth and reduction of excessive hair loss.

Lower alkyl esters of nicotinic acid are known to be vasodilators. However, such esters as methyl, ethyl and propyl nicotinate have been found to be excessively irritating to skin tissues when applied topically in amounts sufficient to produce desired levels of dilation, on the order of from about 1 to about 10 percent in such carriers as vasoline, petrolatum and the like. The disclosure of Huber in U.S. Pat. No. 2,431,558 indicates that topical application of lower alkyl esters of nicotinic acid results in inflammation, irritation and, in some instances, edema or eczema.

It has been found that the combination of lower alkyl nicotinates and histamine hydrochloride provides for a composition exhibiting a synergistic effect in attaining superior results while using a lower concentration of nicotinate-histamine with no irritation, edema or eczema resulting during topical use.

The lower alkyl esters of nicotinic acid include methyl, ethyl, propyl and butyl nicotinates, or mixtures thereof.

It is believed that the combination of lower alkyl nicotinate and histamine hydrochloride exerts a stimulating effect on the zymogens which control hair growth, increasing hair growth and lessening or preventing excessive hair loss.

In accordance with the invention, there is provided a scalp treating and hair growth promoting composition comprising from about 1 to about 3 percent by weight lower alkyl nicotinate and from about 0.005 to about 5.0 percent by weight histamine hydrochloride in a pharmaceutically acceptable vehicle.

The composition may be formulated in the form of solutions, emulsions, suspensions, lotions, ointments, and gels, and may contain adjuvants, such as bacteriocides or bacteriostats, perfume, vitamins, surface active agents and the like. Such carriers as water, mineral oil, lanolin, lanolin derivatives, waxes, gelling agents, or suitable solvents such as aliphatic alcohols and the like may be employed to formulate stable solutions, lotions, gels and the like for topical application to the hair and scalp.

The carrier employed, as previously stated, may be water, mineral oil, lanolin, lanolin derivatives, waxes gelling agents, lower aliphatic alcohols and the like. Suitable alcohols include inter alia, the lower aliphatic alcohols, such as methanol, ethanol, propanol, isopropanol and the like. Polyhydric alcohols which may be advantageously employed include lower alkylene glycols such as ethylene glycol, propylene glycol, glycerol and the like.

Vitamins such as A, D and E may be added to the formulation, if desired, in amounts of about 0.02 to 0.06 percent by weight, either singly or in various combinations, as hair texturing agents.

Bacteriocides and bacteriostats, when use, may be any compound or compounds compatible with the active ingredients, possessing the desired properties, among which may be mentioned, benzonium chloride, parabin and the like.

The bacteriocides and bacteriostats, when use, are incorporated int he compositions in bacteriocidally or bacteriostatically effect amounts, generally on the order of from about 0.01 to about 1.0 percent by weight.

Suitable detergents or surface active agents include the anionic, cationic and nonionic surfactants.

Anionic surfactants include the alkali metal salts of sulfated fatty alcohols having from 8 to 18 carbon atoms, alkali metal salts of sulfated fatty acid amides having 8 to 18 carbon atoms, and the like.

Non-ionic surfactants include alkylamine oxides having 8 to 18 carbon atoms, such as lauryl-dimethylamine oxide, cetyldimethylamine oxide and the like; fatty acid mono- and dialkanol amides such as lauric monoethanolamine, stearic diethanolamide and the like; polyethylene oxide condensates; condensates of fatty acids, fatty alcohols, and fatty hydroxy acids with alkylene oxides; and the like.

Suitable cationic surfactants include the quaternary ammonium compounds of mono- and di-alkylamines having 8 to 18 carbon atoms in the alkyl chain, such as hexyl-trimethyl ammonium chloride, octyl trimethyl ammonium chloride, dicoco dimethyl ammonium chloride, and the like.

The use of surfactants in cosmetic formulations is well known, with the surfactants employed in effective amounts, that is, in amounts sufficient to provide a stable composition having skin and hair conditioning properties. Generally, from about 0.1 to about 20 percent by weight and preferably from about 0.5 to about 1.0 percent by weight of a selected surfactant, or mixtures thereof, based on the total weight of the final compositions, has been found to be satisfactory. Excessive amounts of surfactant tend to produce foams which are sticky and tacky to the touch, while insufficient amounts of surfactant provide products having insufficient activity and skin and hair conditioning power.

obtained by experimentation in which adult males ranging in age, as previously stated, from 25 to 65 were treated for definite periods with compositions containing histamine hydrochloride, methyl nicotinate and histamine hydrochloride/methyl nicotinate in varying concentrations, with all other constituents of the compositions used present in unvarying amounts. The test results were achieved by application of each formulation to each subject twice daily for the period indicated, each application consisting of dispensing from 0.5 to 3 ml of formulation to the scalp and hair and manual stimulation of the covered areas for periods from about 15 seconds to one minute.

The following compositions were utilized to obtain the data set forth in Table I:

TABLE I

| COMPONENT | Formulation No.; pct/wgt | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Histamine dihydrochloride | — | — | — | — | — | — | — | 0.1 | 0.5 | 1.0 | 3.0 | 5.0 | 0.1 | 0.1 | 0.5 |
| Methyl nicotinate | — | 0.5 | 1.0 | 3.0 | 5.0 | 8.0 | 10.0 | — | — | — | — | — | 1.0 | 3.0 | 3.0 |
| Lecithin | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Inositol | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Biotin | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Petrolatum | 97.89 | 97.30 | 96.89 | 94.89 | 92.89 | 89.89 | 87.89 | 97.79 | 97.39 | 96.89 | 94.89 | 92.89 | 97.29 | 94.79 | 94.39 |

The compositions of the present invention are formulated to a pH in the range of from about 4 to about 7.9, preferably about 7. Control of the pH may be effected by incorporating buffering agents in the formulation. Any compatible buffering agent generally finding application in the pharmaceutical arts may be used, such as the inorganic phosphates and borates, and the like, employed in amounts sufficient to obtain the desired pH.

Formulations of the compositions is effected by simple admixture of the various components in no particular sequence. Generally, the constituents are simply mixed for a period of time sufficient to obtain an essentially homogenous blend. For example, utilizing a mechanical stirrer, water and glycerin were mixed. Thereafter, lecithin, inositol and biotin were added. Histamine dihydrochloride and methyl nicotinate were added slowly to this composition, and petrolatum incorporated to yield a yellow ointment having the following composition:

Histamine dihydrochloride:0.1
Methyl nicotinate:1.0
Lecithin: 1.0
Inositol:1.0
Biotin:0.05
Petrolatum:rem.

In use, the compositions are topically applied to the scalp and hair with massaging in the area or areas to be treated, with application effected once or twice daily in relatively small amounts, on the order of from about 0.5 to 3 ml of composition being sufficient.

Experimental data, obtained by treatment of adult males ranging in age from 25 to 65, each with pattern baldness or excessive hair loss histories, indicates that the histamine hydroohloride - alkyl nicotinate compositions described hereinabove function to prevent hair loss and stimulate new hair growth. However, experimental data obtained also indicates that compositions containing either histamine hydrochloride or alkyl nicotinate, but not both, are ineffective, even in increased concentrations, suggesting that the effect created by the combination of histamine hydrochloride and alkyl nicotinate is of a synergistic nature. The following data was The results obtained are set forth in Table II:

TABLE II

| COMP. NO. | SUBJECT-APPLICATION DAYS | | | | | | RESULTS |
|---|---|---|---|---|---|---|---|
| | 1 | 2 | 3 | 4 | 5 | 6 | |
| 1 | 5 | 5 | 5 | 5 | 5 | 5 | b |
| 2 | 5 | 5 | 5 | 5 | 5 | 5 | c |
| 3 | 5 | 5 | 5 | 5 | 5 | 5 | c |
| 4 | 5 | 5 | 5 | 5 | 5 | 5 | c |
| 5 | 5 | 5 | 5 | 5 | 5 | 5 | c |
| 6 | 5 | 5 | 5 | 5 | 5 | 5 | c |
| 7 | 5 | 5 | 5 | 5 | 5 | 5 | c |
| 8 | 5 | 5 | 5 | 5 | 5 | 5 | c |
| 9 | 5 | 5 | 5 | 5 | 5 | 5 | c |
| 10 | 1 | 1 | 1 | 1 | 1 | 1 | a |
| 11 | 1 | 1 | 1 | 1 | 1 | 1 | a |
| 12 | 1 | 1 | 1 | 1 | 1 | 1 | a |
| 13 | 5 | 5 | 5 | 5 | 5 | 5 | e |
| 14 | 5 | 5 | 5 | 5 | 5 | 5 | d |
| 15 | 5 | 5 | 5 | 5 | 5 | 5 | d | a = headaches, each subject, discontinued.
b = no activity noted.
c = vasodilation, no reduction hair loss, no new growth.
d = vasodilation, hair loss substantially eliminated by 3rd day.
e = same results as (d); results continued to be excellent over additional 40 test period; new growth noted after 14 days.

It is to be understood that the foregoing Examples are offered as illustrations of the preferred embodiments of the present invention that various changes may be made without departing from the scope thereof.

I claim:

1. A composition to promote hair growth to be applied topically to hair and scalp in ointment form consisting essentially of about 0.1 parts by weight histamine hydrochloride, 1.0 parts by weight of methyl nicotinate, 1.0 parts by weight lecithin, 1.0 parts by weight inositol, 0.05 biotin, and about 96.9 parts by weight petrolatum.

2. A method to promote hair growth comprising applying to the hair and the scalp a composition consisting essentially of from about 0.005 to about 5.0 parts by weight histamine hydrochloride and from about 0.5 to about 3.0 parts by weight of a carbon alkyl nicotinate said lower carbon alkyl nicotinate selected from the group consisting of methyl, ethyl, propyl and butyl nicotinate said composition including sufficient pharmaceutically acceptable carrier or solvent to form a solution, emulsion, suspension, lotion, ointment or gel.

3. A method according to claim 2, wherein said alkyl nicotinate is methyl nicotinate.

4. A method as defined in claim 2, additionally containing a bacteriostat selected from the group consisting of benzonium chloride and parabin present in bacteriostatically effect amounts.

5. A method according to claim 2, where the histamine hydrochloride is present in an amount of about 0.1 parts by weight and the carbon alkyl nicotinate is present in an of about 1.0 parts by weight.

6. A method to promote hair growth comprising applying to the hair and the scalp a composition consisting essentially of about 0.1 parts by weight histamine hydrochloride, 1.0 parts by weight of methyl nicotinate, 1.0 parts by weight lecithin, 1.0 parts by weight inositol, 0.05 biotin, and about 96.9 parts by weight petrolatum.

* * * * *